(12) United States Patent
Imaizumi (10) Patent No.: US 9,872,602 B2
(45) Date of Patent: Jan. 23, 2018

(54) OPTICAL SCANNING TYPE OBSERVATION APPARATUS AND METHOD FOR OPERATING OPTICAL SCANNING TYPE OBSERVATION APPARATUS

(71) Applicant: OLYMPUS CORPORATION, Tokyo (JP)

(72) Inventor: Katsuichi Imaizumi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/249,606

(22) Filed: Aug. 29, 2016

(65) Prior Publication Data

US 2016/0367109 A1     Dec. 22, 2016

Related U.S. Application Data

(63) Continuation of application No. PCT/JP2015/055843, filed on Feb. 27, 2015.

(30) Foreign Application Priority Data

May 28, 2014   (JP) .................................. 2014-110407

(51) Int. Cl.
*A61B 1/04*     (2006.01)
*A61B 1/06*     (2006.01)
(Continued)

(52) U.S. Cl.
CPC ...... *A61B 1/00009* (2013.01); *A61B 1/00006* (2013.01); *A61B 1/00165* (2013.01);
(Continued)

(58) Field of Classification Search
CPC ............ A61B 1/00009; A61B 1/00006; A61B 1/00165; A61B 1/00172; A61B 1/04;
(Continued)

(56) References Cited

U.S. PATENT DOCUMENTS

| 5,243,666 A | 9/1993 | Hasegawa et al. |
| 2008/0226029 A1* | 9/2008 | Weir ........................ A61B 1/07 378/65 |

(Continued)

FOREIGN PATENT DOCUMENTS

| JP | H03-147488 A | 6/1991 |
| JP | 2008-272033 A | 11/2008 |

(Continued)

OTHER PUBLICATIONS

International Search Report dated May 19, 2015 issued in PCT/JP2015/055843.

(Continued)

*Primary Examiner* — John P Leubecker
(74) *Attorney, Agent, or Firm* — Scully, Scott, Murphy & Presser, P.C.

(57) ABSTRACT

An optical scanning type observation apparatus includes: a light source portion for supplying illuminating light; an optical fiber for guiding the illuminating light and emitting the illuminating light from an emission end portion; an actuator portion for displacing an irradiation position of the illuminating light by swinging the emission end portion; a control portion for controlling the actuator portion such that at least a first frame and a second frame are periodically obtained; an image generating portion for sequentially generating at least a first image in the first frame and a second image in the second frame; a motion detecting portion for detecting a motion of an image between different frames; and an image outputting portion for outputting one or both of the first and second images based on a motion detected by the motion detecting portion.

6 Claims, 5 Drawing Sheets

(51) Int. Cl.
*A61B 1/00* (2006.01)
*A61B 1/07* (2006.01)

(52) U.S. Cl.
CPC ............ *A61B 1/00172* (2013.01); *A61B 1/04* (2013.01); *A61B 1/042* (2013.01); *A61B 1/0669* (2013.01); *A61B 1/07* (2013.01)

(58) Field of Classification Search
CPC ......... A61B 1/042; A61B 1/0669; A61B 1/07; A61B 5/0062; G02B 26/103
See application file for complete search history.

(56) References Cited

U.S. PATENT DOCUMENTS

| | | | |
|---|---|---|---|
| 2008/0291597 A1 | 11/2008 | Seibel et al. | |
| 2010/0137684 A1* | 6/2010 | Shibasaki | A61B 1/00009 600/109 |
| 2010/0157037 A1* | 6/2010 | Iketani | A61B 1/00009 348/68 |
| 2013/0155215 A1* | 6/2013 | Shimada | A61B 1/00172 348/68 |
| 2014/0180012 A1* | 6/2014 | Yoshino | A61B 1/00006 600/180 |
| 2014/0184768 A1* | 7/2014 | Hasegawa | G02B 23/26 348/68 |

FOREIGN PATENT DOCUMENTS

| | | |
|---|---|---|
| JP | 2010-142482 A | 7/2010 |
| JP | 2010-527688 A | 8/2010 |
| WO | WO 2008/143823 A1 | 11/2008 |

OTHER PUBLICATIONS

Japanese Office Action dated Jan. 26, 2016 issued in JP 2015-550880.

* cited by examiner

OPTICAL SCANNING TYPE OBSERVATION APPARATUS AND METHOD FOR OPERATING OPTICAL SCANNING TYPE OBSERVATION APPARATUS

CROSS REFERENCE TO RELATED APPLICATION

This application is a continuation application of PCT/JP2015/055843 filed on Feb. 27, 2015 and claims benefit of Japanese Application No. 2014-110407 filed in Japan on May 28, 2014, the entire contents of which are incorporated herein by this reference.

BACKGROUND OF THE INVENTION

1. Field of the Invention

The present invention relates to an optical scanning type observation apparatus and a method for operating the optical scanning type observation apparatus, and in particular to an optical scanning type observation apparatus for scanning an object to generate an image and a method for operating the optical scanning type observation apparatus.

2. Description of the Related Art

For endoscopes in a medical field, various techniques for reducing a diameter of an insertion portion inserted into a body cavity of a subject are proposed to reduce a burden on the subject. As an example of such techniques, a scanning type endoscope not having a solid image pickup device at a part corresponding to the insertion portion described above and an observation apparatus configured having the scanning type endoscope are known.

More specifically, the observation apparatus having the scanning type endoscope is configured, for example, to two-dimensionally scan an object in a scan pattern set in advance by causing a distal end portion of an illumination fiber for guiding illuminating light emitted from a light source to be swung, receive return light from the object by a receiving fiber arranged around the illumination fiber, and generate an image of the object based on the return light received by the receiving fiber. As such that has a configuration similar to the configuration of the observation apparatus, for example, an optical scanning type endoscope apparatus disclosed in Japanese Patent Application Laid-Open Publication No. 2010-142482 is known.

More specifically, Japanese Patent Application Laid-Open Publication No. 2010-142482 discloses a configuration of an optical scanning type observation apparatus provided with such a light supply fiber that a position of an emission end in a state of not being bent is set at a predetermined reference point, the configuration being for performing such control that a scanning period during which a distal end of the light supply fiber is caused to be displaced along a spiral-shaped displacement route, from the predetermined reference point to a maximum amplitude, and a damping period during which the light supply fiber is caused to be displaced from the maximum amplitude to the predetermined reference point are alternately repeated. Further, Japanese Patent Application Laid-Open Publication No. 2010-142482 also discloses a configuration for performing radiation of white color light to an observation target area and generation of a pixel signal during the scanning period.

SUMMARY OF THE INVENTION

An optical scanning type observation apparatus of an aspect of the present invention includes: a light source portion configured to supply illuminating light; an optical fiber configured to guide the illuminating light incident from an incident end portion connected to the light source portion and emit the illuminating light from an emission end portion to an object, and to allow swinging the emission end portion; an actuator portion configured to cause an irradiation position of the illuminating light emitted to the object via the light guiding portion to be displaced by swinging the emission end portion; a control portion configured to control the actuator portion such that at least a first frame and a second frame are periodically obtained, a first scan route being drawn at the irradiation position in the first frame, a second scan route different from the first scan route being drawn at the irradiation position in the second frame; an image generating portion configured to sequentially generate at least a first image in the first frame and a second image in the second frame, based on a signal obtained by receiving return light from the object to which the illuminating light is radiated; a motion detecting portion configured to detect a motion of an image between different frames generated by the image generating portion; and an image outputting portion configured to, based on a motion detected by the motion detecting portion, output one of the first and second images or output both of the first and second images.

A method for operating an optical scanning type observation apparatus of an aspect of the present invention includes: a supply step of the optical scanning type observation apparatus supplying illuminating light; an emission step of the optical scanning type observation apparatus guiding the illuminating light incident from an incident end portion of an optical fiber and emitting the illuminating light from an emission end portion of the optical fiber to an object; a displacement step of the optical scanning type observation apparatus causing an irradiation position of the illuminating light emitted to the object to be displaced by swinging the emission end portion; a control step of the optical scanning type observation apparatus controlling the emission end portion such that at least a first frame and a second frame are periodically obtained, a first scan route being drawn at the irradiation position in the first frame, a second scan route different from the first scan route being drawn at the irradiation position in the second frame; a generation step of the optical scanning type observation apparatus sequentially generating at least a first image in the first frame and a second image in the second frame, based on a signal obtained by receiving return light from the object to which the illuminating light is radiated; a detection step of the optical scanning type observation apparatus detecting a motion of an image between different frames generated in the generation step; and an output step of the optical scanning type observation apparatus, based on a motion detected in the detection step, outputting one of the first and second images or outputting both of the first and second images.

DETAILED DESCRIPTION OF THE PREFERRED EMBODIMENT(S)

An embodiment of the present invention will be described below with reference to drawings.

Figure 1:
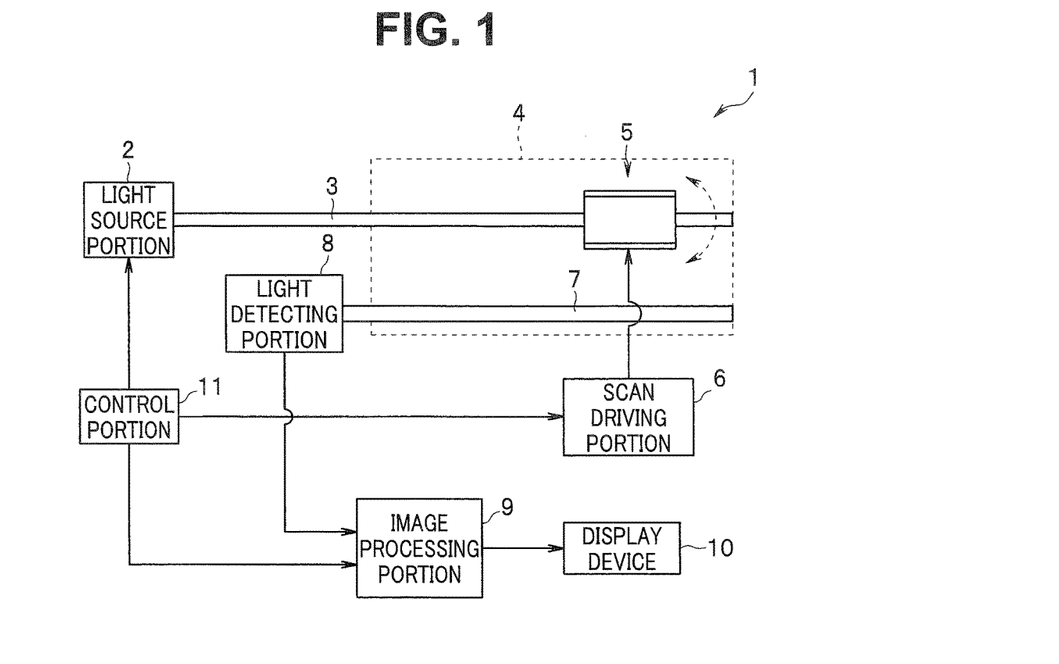
FIG. 1 is a diagram showing a configuration of main parts of an optical scanning type observation apparatus according to an embodiment.

FIGS. 1 to 7 relate to the embodiment of the present invention. FIG. 1 is a diagram showing a configuration of main parts of an optical scanning type observation apparatus according to the embodiment.

For example, as shown in FIG. 1, an optical scanning type observation apparatus 1 is configured having a light source portion 2, an optical fiber 3, a scanning type endoscope 4, an actuator portion 5, a scan driving portion 6, an optical fiber bundle 7, a light detecting portion 8, an image processing portion 9, a display device 10 and a control portion 11.

The light source portion 2 is configured to be capable of generating illuminating light for illuminating an object and supply the illuminating light to the optical fiber 3. Further, the light source portion 2 is configured to perform or stop supply of the illuminating light to the optical fiber 3 by being turned on or off based on control of the control portion 11. More specifically, the light source portion 2 is provided with, for example, a red color (R) light laser light source, a green color (G) light laser light source and a blue color (B) light laser light source which can be switched between a light emission state (on state) and a light extinction state (off state) according to control of the control portion 11 and configured to be capable of supplying white color light generated by mixing R light, G light and B light to the optical fiber 3 as illuminating light.

The optical fiber 3 is configured, for example, with a single-mode fiber. An incident end portion of the optical fiber 3, which includes a light incident face, is connected to the light source portion 2. Further, an emission end portion of the optical fiber 3, which includes a light emission face, is arranged at a distal end portion of the scanning type endoscope 4. That is, the optical fiber 3 is configured to be capable of guiding illuminating light supplied by the light source portion 2 and emitting the guided illuminating light to an object from the emission end portion.

The scanning type endoscope 4 is configured having an elongated shape insertable into a body cavity of the subject. Inside the scanning type endoscope 4, each of the optical fiber 3 and the optical fiber bundle 7 is inserted. Further, inside the scanning type endoscope 4, the actuator portion 5 is provided which is configured to swing the emission end portion of the optical fiber 3 in response to a driving signal supplied from the scan driving portion 6.

Figure 2:
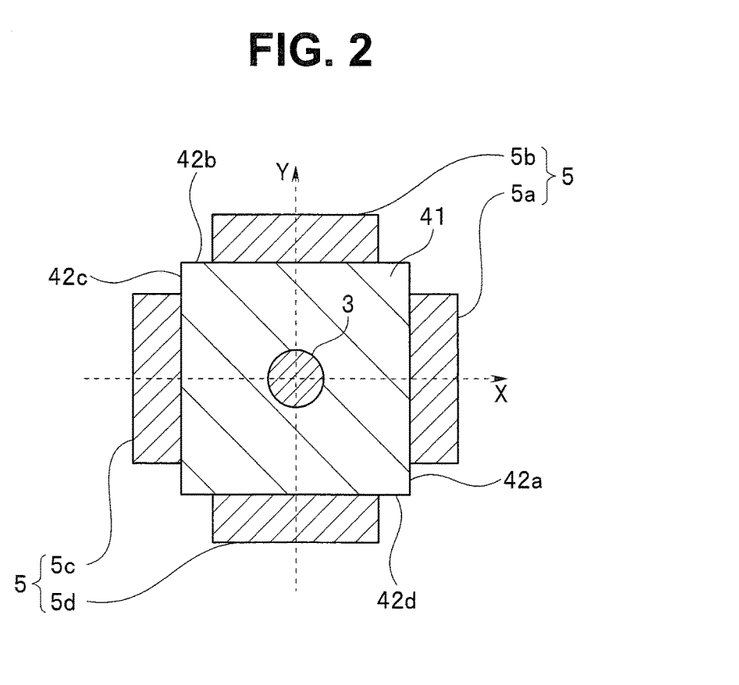
FIG. 2 is a cross-sectional view for illustrating a configuration of an actuator portion provided in a scanning type endoscope.

On the other hand, each of the optical fiber 3 and the actuator portion 5 is arranged so as to have a positional relationship, for example, shown in FIG. 2 on a section which is vertical in a longitudinal axis direction of the scanning type endoscope 4. FIG. 2 is a cross-sectional view for illustrating the configuration of the actuator portion provided in the scanning type endoscope.

As shown in FIG. 2, a ferrule 41 as a joining member is arranged between the optical fiber 3 and the actuator portion 5. More specifically, the ferrule 41 is formed, for example, with zirconia (ceramics) or nickel.

As shown in FIG. 2, the ferrule 41 is formed as a quadrangular prism and has sides 42a and 42c vertical to an X axis direction, which is a first axis direction orthogonal to the longitudinal axis direction of the scanning type endoscope 4 and sides 42b and 42d vertical to a Y axis direction, which is a second axis direction orthogonal to the longitudinal axis direction of the scanning type endoscope 4. Further, the optical fiber 3 is fixedly arranged at a center of the ferrule 41. Note that the ferrule 41 may be fondled in a shape other than the quadrangular prism as far as the ferrule 41 has a pillar shape.

As shown in FIG. 2, the actuator portion 5 has a piezoelectric element 5a arranged along the side 42a, a piezoelectric element 5b arranged along the side 42b, a piezoelectric element 5c arranged along the side 42c, and a piezoelectric element 5d arranged along the side 42d.

The piezoelectric elements 5a to 5d have polarization directions set in advance individually and are configured to expand or contract in response to a driving signal supplied from the scan driving portion 6.

The scan driving portion 6 is configured to, based on control of the control portion 11, generate and output a driving signal for causing the actuator portion 5 to be driven.

Figure 3:
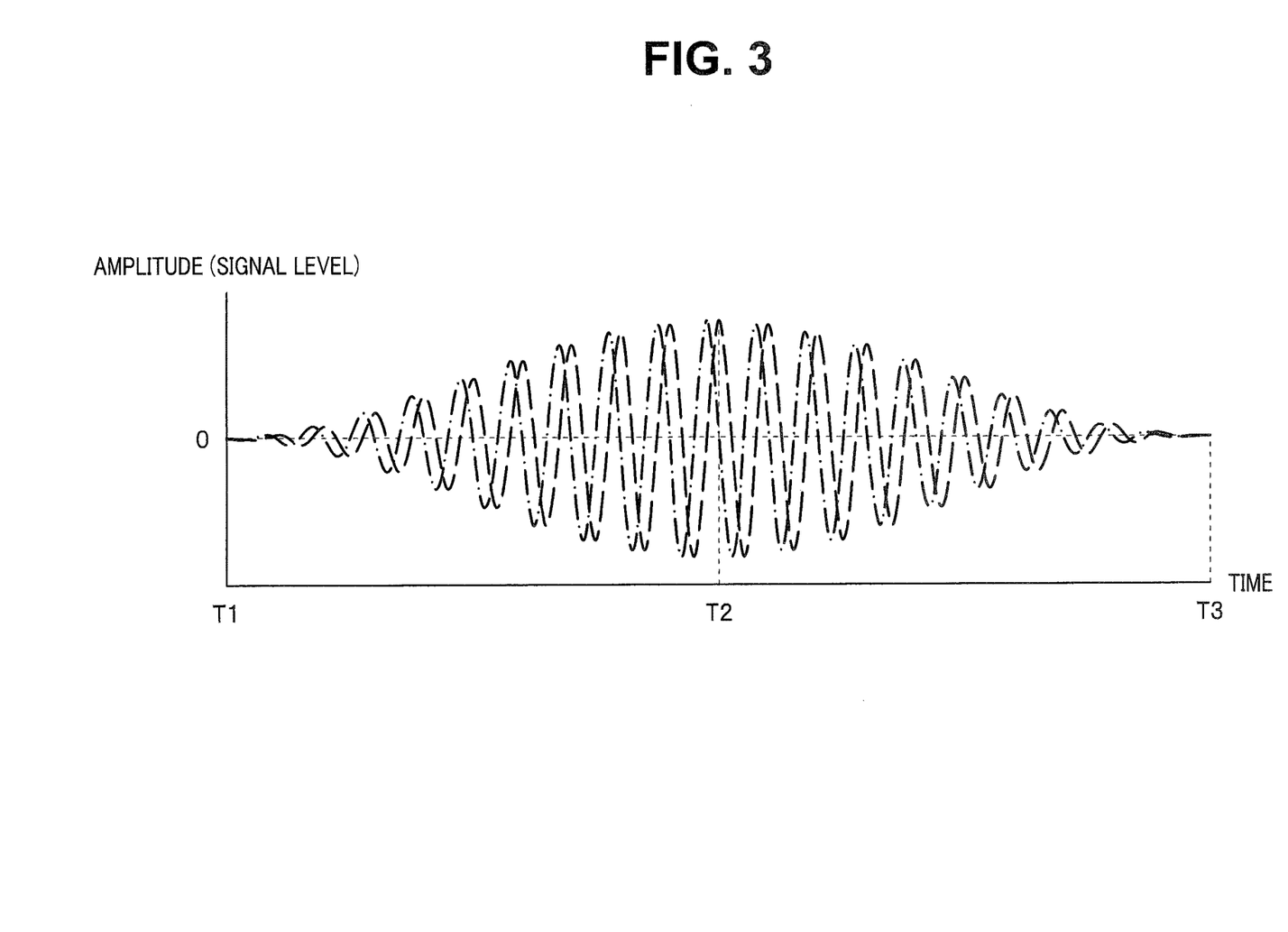
FIG. 3 is a diagram showing an example of a signal waveform of a driving signal supplied to the actuator portion of the scanning type endoscope.

More specifically, the scan driving portion 6 generates a signal having a waveform obtained by performing predetermined modulation for a sine wave, for example, as shown by a broken line in FIG. 3 as a first driving signal for causing the emission end portion of the optical fiber 3 to be swung along the X axis direction and outputs the signal to the actuator portion 5. Further, the scan driving portion 6 generates a signal having a waveform obtained by displacing a phase of the first driving signal by 90°, for example, as shown by a long dashed short dashed line in FIG. 3 as a second driving signal for causing the emission end portion of the optical fiber 3 to be swung along the Y axis direction and outputs the signal to the actuator portion 5. FIG. 3 is a diagram showing an example of the signal waveforms of the driving signals supplied to the actuator portion of the scanning type endoscope.

Figure 4:
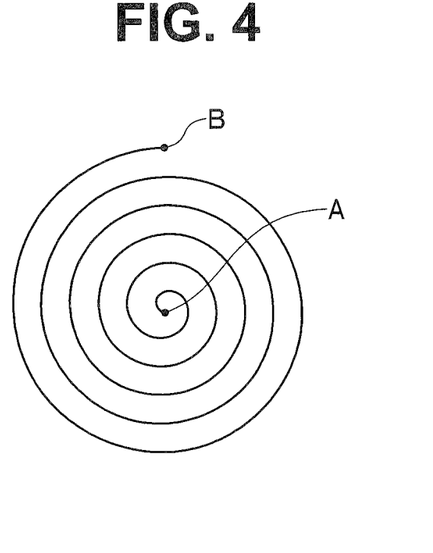
FIG. 4 is a diagram for illustrating temporal displacement of an illuminating light irradiation position from a point A to a point B.
Figure 5:
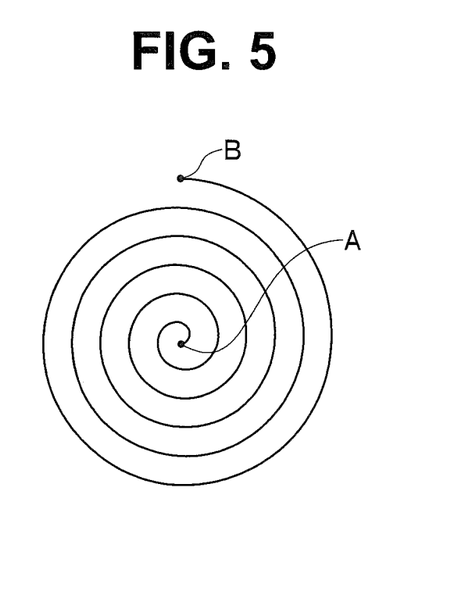
FIG. 5 is a diagram for illustrating temporal displacement of the illuminating light irradiation position from the point B to the point A.

Here, for example, by the first driving signal having a signal waveform as shown by the broken line in FIG. 3 being supplied to the piezoelectric elements 5a and 5c of the actuator portion 5 and the second driving signal having a signal waveform as shown by the long dashed short dashed line in FIG. 3 being supplied to the piezoelectric elements 5b and 5d of the actuator portion 5, the emission end portion of the optical fiber 3 is swung in a spiral shape, and, in response to such a swing, a surface of an object is scanned in a spiral shape as shown in FIGS. 4 and 5. FIG. 4 is a diagram for illustrating temporal displacement of an illuminating light irradiation position from a point A to a point B. FIG. 5 is a diagram for illustrating temporal displacement of an illuminating light irradiation position from the point B to the point A.

More specifically, first, at a time T1, illuminating light is radiated to a position corresponding to the point A which is a center point of the illuminating light irradiation position on the surface of the object. After that, accompanying amplitude values of the first and second driving signals increasing during a period from the time T1 to time T2, the illuminating light irradiation position on the surface of the object is displaced so that a first spiral-shaped scan route is drawn to an outside with the point A as a starting point. Furthermore, when the time T2 is reached, the illuminating light is radiated to the point B which is an outermost point of the illuminating light irradiation position on the surface of the object. Then, accompanying the amplitude values of the first and second driving signals decreasing during a period from the time T2 to time T3, the illuminating light irradiation position on the surface of the object is displaced so that a second spiral-shaped scan route is drawn to an inside with the point B as a starting point. Furthermore, when the time T3 is reached, the illuminating light is radiated to the point A on the surface of the object.

That is, the actuator portion 5 has a configuration capable of causing the irradiation position of the illuminating light emitted to the object via the emission end portion to be displaced along the spiral-shaped scan routes shown in FIGS. 4 and 5 by swinging the emission end portion of the optical fiber 3 based on the first and second driving signals supplied from the scan driving portion 6.

The optical fiber bundle 7 is configured, for example, by a plurality of optical fibers being bundled. An incident end portion of the optical fiber bundle 7 is arranged at the distal end portion of the scanning type endoscope 4. An emission end portion of the optical fiber bundle 7, which includes a light emission face, is connected to the light detecting portion 8. That is, the optical fiber bundle 7 is configured to be capable of receiving return light (reflected light) from the object at the distal end portion of the scanning type endoscope 4 and guiding the received return light to the light detecting portion 8.

The light detecting portion 8 is configured having, for example, an avalanche photodiode and an A/D converter. The light detecting portion 8 is configured to generate an electric signal corresponding to an amount of return light caused to be incident via the optical fiber bundle 7, convert the generated electric signal to a digital signal and sequentially output the digital signal.

Figure 6:
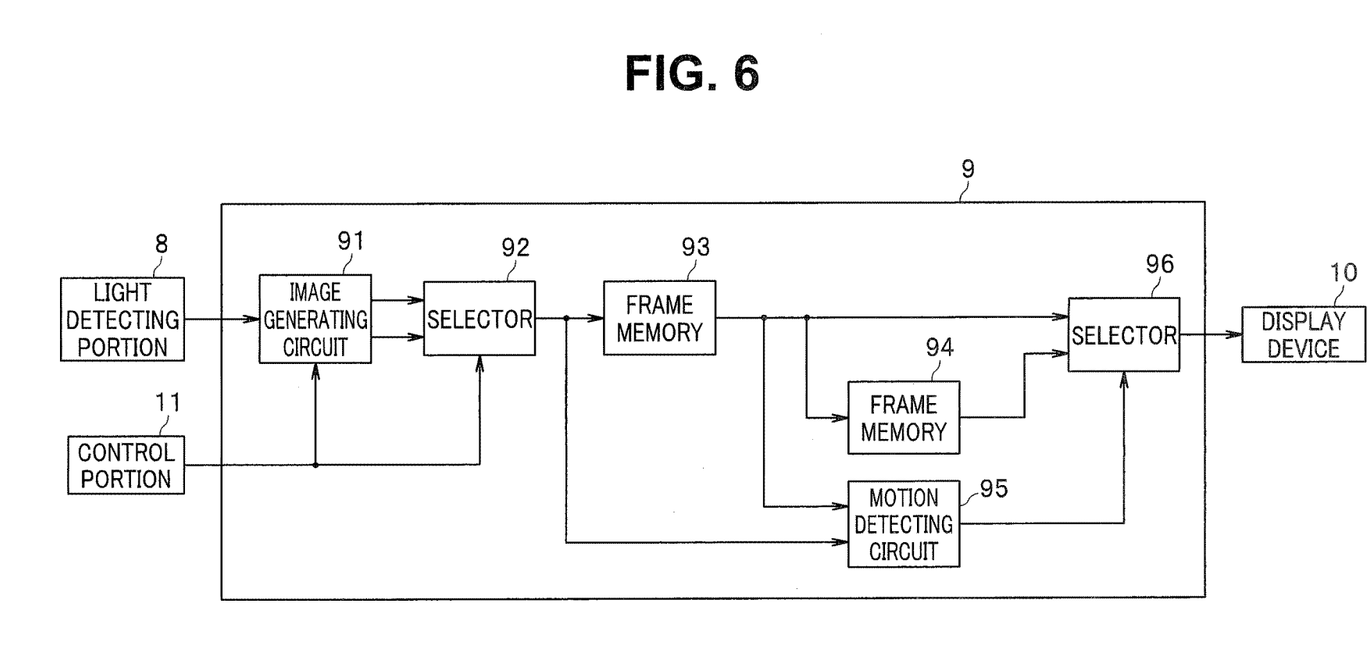
FIG. 6 is a diagram for illustrating an example of a specific configuration of an image processing portion included in the optical scanning type observation apparatus according to the embodiment.

For example, as shown in FIG. 6, the image processing portion 9 is configured having an image generating circuit 91, a selector 92, frame memories 93 and 94, a motion detecting circuit 95 and a selector 96. FIG. 6 is a diagram for illustrating an example of a configuration of the image processing portion included in the optical scanning type observation apparatus according to the embodiment.

The image generating circuit 91 is configured to, based on control of the control portion 11, map luminance values shown by the digital signals outputted from the light detecting portion 8 to generate an image corresponding to one frame and sequentially outputs the generated image corresponding to one frame to the selector 92.

More specifically, the image generating circuit 91 is configured to, based on control of the control portion 11, identify raster-format pixel positions corresponding to illuminating light irradiation positions on the first spiral-shaped scan route when scanning of an object is performed along the first spiral-shaped scan route shown in FIG. 4, maps the luminance values shown by the digital signals sequentially outputted from the light detecting portion 8 onto the identified pixel positions to generate an outward image Ff corresponding to one frame, and sequentially output the generated outward image Ff to the selector 92. Further, the image generating circuit 91 is configured to, based on control of the control portion 11, identify raster-format pixel positions corresponding to illuminating light irradiation positions on the second spiral-shaped scan route when scanning of the object is performed along the second spiral-shaped scan route shown in FIG. 5, maps the luminance values shown by the digital signal sequentially outputted from the light detecting portion 8 onto the identified pixel positions to generate an inward image Fb corresponding to one frame, and sequentially output the generated inward image Fb to the selector 92.

The selector 92 is configured to, based on control of the control portion 11, output images outputted from the image generating circuit 91 one frame by one frame, selectively to the frame memory 93 and the motion detecting circuit 95.

More specifically, the selector 92 is configured to, based on control of the control portion 11, output the outward image Ff outputted from the image generating circuit 91 to the frame memory 93 and the motion detecting circuit 95, for example, when scanning of the object is performed along the first spiral-shaped scan route shown in FIG. 4. Further, the selector 92 is configured to, based on control of the control portion 11, output the inward image Fb outputted from the image generating circuit 91 to the frame memory 93 and the motion detecting circuit 95, for example, when scanning of the object is performed along the second spiral-shaped scan route shown in FIG. 5.

The frame memory 93 is configured having, for example, a FIFO (first-in, first-out) memory capable of storing an image corresponding to one frame. Further, the frame memory 93 is configured to store an image corresponding to one frame outputted from the selector 92 and output an image corresponding to one frame which has been stored before storing the image to the frame memory 94, the motion detecting circuit 95 and the selector 96.

The frame memory 94 is configured having, for example, a FIFO memory capable of storing an image corresponding to one frame. Further, the frame memory 94 is configured to store an image corresponding to one frame outputted from the frame memory 93 and output an image corresponding to one frame which has been stored before storing the image to the selector 96. That is, the frame memory 94 stores an image generated by the image generating circuit 91 one frame before an image stored in the frame memory 93.

For example, the motion detecting circuit 95 is configured to detect a motion vector between an image corresponding to one frame outputted from the frame memory 93 and an image corresponding to one frame outputted from the selector 92 and calculate a magnitude of the detected motion vector as an amount of motion corresponding to one frame. Further, the motion detecting circuit 95 is configured to, when detecting that the amount of motion corresponding to one frame calculated as described before exceeds a predetermined threshold TH, control the selector 96 to select output from either the frame memory 93 or the frame memory 94 and not to select output from the other between the frame memory 93 and the frame memory 94. Further, the motion detecting circuit 95 is configured to, when detecting that the amount of motion corresponding to one frame calculated as described before is equal to or below the predetermined threshold TH, control the selector 96 to alternately select the output from the frame memory 93 and the output from the frame memory 94.

The selector 96 has a function as an image outputting portion and is configured to, based on control of the motion detecting circuit 95, output images outputted from the frame memories 93 and 94 selectively to the display device 10.

The display device 10 is configured, for example, with a liquid crystal display. Further, the display device 10 is configured to be capable of displaying an image and the like outputted from the image processing portion 9.

The control portion 11 is configured having, for example, a CPU. Further, the control portion 11 is configured to control the light source portion 2 and the scan driving portion 6 to cause them to scan the object, for example, along the first spiral-shaped scan route shown in FIG. 4 and the second spiral-shaped scan route shown in FIG. 5. Further, the control portion 11 is configured to control the image generating circuit 91 and the selector 92 according to a latest scan route.

That is, the control portion 11 is configured to control the scan driving portion 6 to cause the emission end portion of the optical fiber 3 to be swung so that such spiral-shaped scan routes are drawn that scan routes for generating images corresponding to two frames are mutually different between the two frames, scan routes for generating images corresponding to odd-numbered frames are mutually same, and scan routes for generating images corresponding to even-numbered frames are mutually same.

Next, operation of the optical scanning type observation apparatus 1 having a configuration as described above will be described.

When detecting that an instruction to start an examination has been made, for example, by an operation of switching on an examination start switch not shown and the like being performed, the control portion 11 repeatedly performs control for causing an object to be scanned along the first spiral-shaped scan route shown in FIG. 4 and the second spiral-shaped route shown in FIG. 5. Then, in response to such control of the control portion 11, the emission end portion of the optical fiber 3 is swung so that the first and second spiral-shaped scan routes are drawn; the object is scanned with illuminating light emitted from the emission end portion of the optical fiber 3; return light from the object is caused to be incident on the light detecting portion 8 through the optical fiber bundle 7; and a digital signal corresponding to the return light is outputted to the image processing portion 9.

Based on control of the control portion 11, the image generating circuit 91 generates and outputs the outward images Ff to the selector 92 one frame by one frame, based on digital signals sequentially outputted from the light detecting portion 8, when the object is being scanned along the first spiral-shaped scan route shown in FIG. 4. Further, based on control of the control portion 11, the image generating circuit 91 generates and outputs inward images Fb to the selector 92 one frame by one frame, based on digital signals sequentially outputted from the light detecting portion 8, when the object is being scanned along the second spiral-shaped scan route shown in FIG. 5. That is, based on control of the control portion 11, the image generating circuit 91 sequentially generates and outputs a current image, which is an image corresponding to one frame, corresponding to a latest scan route between the first spiral-shaped scan route shown in FIG. 4 and the second spiral-shaped scan route shown in FIG. 5.

Based on control of the control portion 11, the selector 92 outputs the outward images Ff outputted from the image generating circuit 91 to the frame memory 93 and the motion detecting circuit 95 when scanning of the object is performed along the first spiral-shaped scan route shown in FIG. 4. Further, based on control of the control portion 11, the selector 92 outputs the inward images Fb outputted from the image generating circuit 91 to the frame memory 93 and the motion detecting circuit 95, for example, when scanning of the object is performed along the second spiral-shaped scan route shown in FIG. 5.

Figure 7:
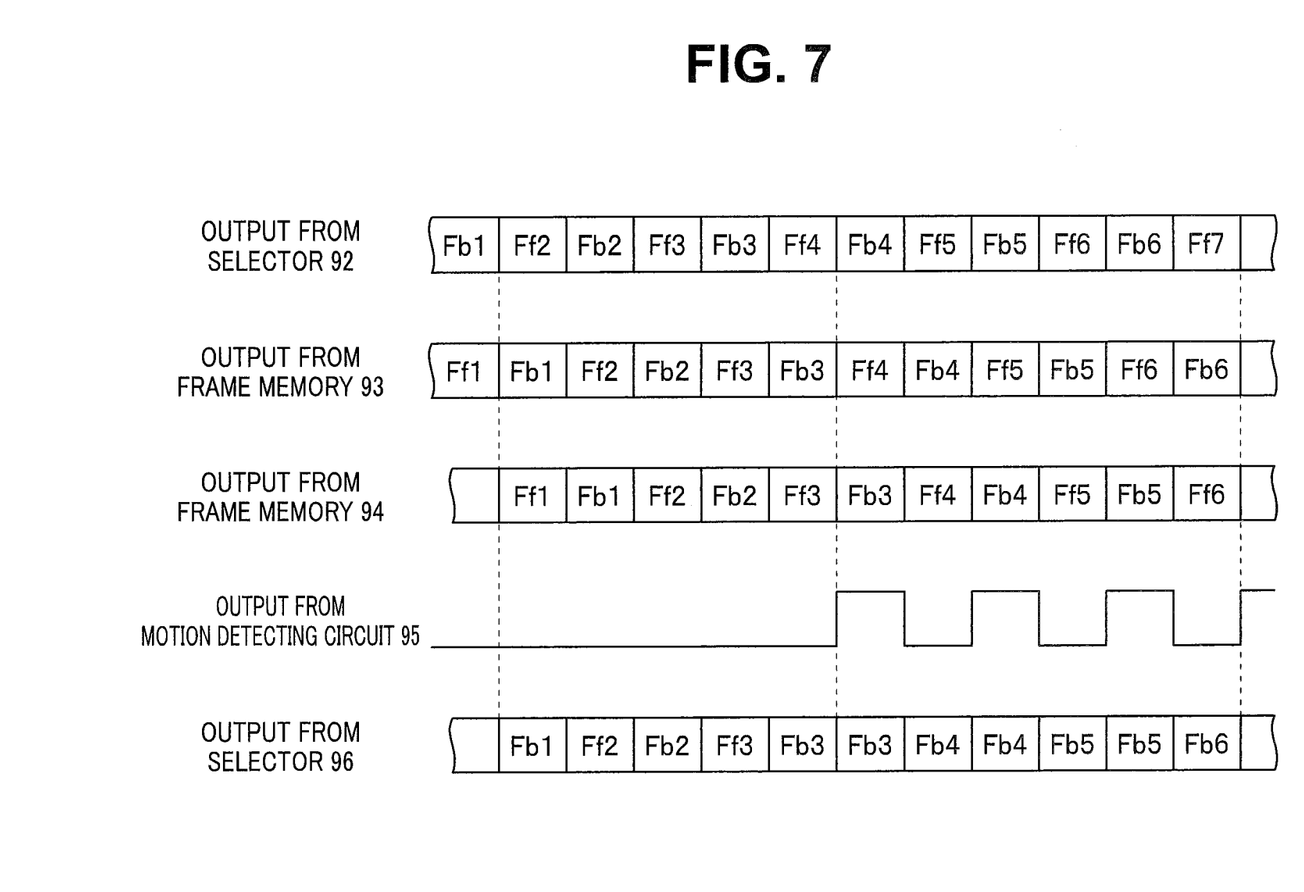
FIG. 7 is a timing chart for illustrating an example of operation of the image processing portion included in the optical scanning type observation apparatus according to the embodiment.

Here, when it is assumed that outward images sequentially outputted one frame by one frame via the selector 92 are indicated by Ffi (i=1, 2, 3, . . . ) and inward images sequentially outputted one frame by one frame via the selector 92 are indicated by Fbj (j=1, 2, 3, . . . ), either an outward image Ffi or an inward image Fbj is stored in the frame memory 93 while an image generated one frame before the image stored in the frame memory 93 is stored in the frame memory 94. FIG. 7 is a timing chart for illustrating an example of operation of the image processing portion included in the optical scanning type observation apparatus according to the embodiment.

On the other hand, the motion detecting circuit 95 detects a motion vector between an image corresponding to one frame outputted from the frame memory 93 and an image corresponding to one frame outputted from the selector 92, calculates a magnitude of the detected motion vector as an amount of motion corresponding to one frame and controls the selector 96 based on the calculated amount of motion corresponding to one frame.

More specifically, when detecting that the amount of motion corresponding to one frame exceeds the predetermined threshold TH, the motion detecting circuit 95 causes output from either the frame memory 93 or the frame memory 94 to be selected and causes output from the other between the frame memory 93 and the frame memory 94 not to be selected, for example, by generating a control signal as shown in FIG. 7 and outputting the control signal to the selector 96. Further, when detecting that the amount of motion corresponding to one frame is equal to or below the predetermined threshold TH, the motion detecting circuit 95 causes output from the frame memory 93 and output from the frame memory 94 to be alternately selected, for example, by generating a control signal as shown in FIG. 7 and outputting the control signal to the selector 96.

For example, as shown in FIG. 7, when the amount of motion corresponding to one frame exceeds the predetermined threshold TH, the selector 96 performs operation for sequentially outputting outward images and inward images to the display device 10 by selecting the output from either the frame memory 93 or the frame memory 94, based on the control of the motion detecting circuit 95. Further, for example, as shown in FIG. 7, when the amount of motion corresponding to one frame is equal to or below the predetermined threshold TH, the selector 96 performs operation for continuously outputting either outward images or inward images two frames by two frames, by alternately selecting output from the frame memory 93 and output from the frame memory 94, based on the control of the motion detecting circuit 95.

As described above, according to the present embodiment, since outward images and inward images are outputted to the display device 10 alternately one frame by one frame when a motion of an object is relatively large, a movie obtained by scanning the object can be displayed at a high frame rate. Further, according to the present embodiment, since either outward images or inward images are continuously outputted to the display device 10 two frames by two frames when a motion of an object is relatively small, it is possible to prevent movie in which the object seems to be in a pseudo-vibration state from being displayed. Therefore, according to the present embodiment, it is possible to cause image quality of movie obtained by scanning an object to be stabilized as far as possible.

Note that the present embodiment is not limited to being applied to the case where control for scanning an object along spiral-shaped scan routes as shown in FIGS. 4 and 5 is performed by the control portion 11 but is almost similarly applied to a case where control for scanning an object along other scan routes, for example, like Lissajous-shaped or raster-shaped scan routes is performed by the control portion 11.

Further, the present embodiment may be appropriately modified to cope with, for example, a case where control for scanning an object along such predetermined scan routes that scan routes at a time of generating images corresponding to P frames (P is an integer equal to or larger than two) are mutually different among the respective P frames, and a scan route at a time of generating an image of a Q-th frame (Q is a natural number) is same as a scan route at a time of generating an image of a Q±n×P-th frame (n is an integer, and Q±n×P is a natural number) is performed by the control portion 11. That is, the spiral-shaped scan routes shown in FIGS. 4 and 5 are scan routes corresponding to a case where a value of P is 2.

In the case of scanning an object along the predetermined scan routes described before, for example, by providing P frame memories F1 to FP capable of causing a current image to be delayed by the number of frames up to P to output the current image to the display device 10, in the image processing portion 9, it is possible for the motion detecting circuit 95 to, when the motion detecting circuit 95 detects that the amount of motion corresponding to one frame exceeds the predetermined threshold TH, control the selector 96 to cause an image generated by the image generating circuit 91 one frame before the current image to be sequentially outputted to the display device 10, and it is possible to, when detecting that the amount of motion corresponding to one frame is equal to or below the threshold TH at the S-th frame (S is a natural number), control the selector 96 to cause images corresponding to a same scan route as a scan rate of the S-th frame to be continuously outputted to the display device 10. (Note that the images outputted to the display device 10 under such control is not limited to the images corresponding to the same scan route as the scan route of the S-th frame but may be images corresponding to a same scan route as a scan route of a frame other than the S-th frame.) More specifically, for example, when continuously detecting that the amount of motion corresponding to one frame is equal to or below the threshold TH for a period corresponding to k (k≥2) frames, the motion detecting circuit 95 acquires a remainder t remaining after dividing k by P and perform control for causing an image t frames before a current image to be outputted to the display device 10. That is, in a case of a scan route for which P=2 is set, like the spiral-shaped scan routes shown in FIGS. 4 and 5, t=1 is always satisfied.

Note that the present invention is not limited to each embodiment described above, and various modifications and applications are, of course, possible within a range not departing from the spirit of the invention.

What is claimed is:

1. An optical scanning type observation apparatus comprising:
   a light source configured to supply illuminating light;
   an optical fiber configured to guide the illuminating light incident from an incident end portion connected to the light source and emit the illuminating light from an emission end portion to an object, and to allow swinging the emission end portion;
   an actuator configured to cause an irradiation position of the illuminating light emitted to the object to be displaced by swinging the emission end portion;
   one or more controllers configured to:
      control the actuator such that at least a first frame and a second frame are periodically obtained, a first scan route being drawn at the irradiation position in the first frame, a second scan route different from the first scan route being drawn at the irradiation position in the second frame;
      generate at least a first image in the first frame and a second image in the second frame, based on a signal obtained by receiving return light from the object to which the illuminating light is radiated;
      detect a motion of an image between different frames; and
      based on a detected motion, output one of the first and second images or output both of the first and second images;
   wherein the actuator is controlled so as to alternately obtain the first and second frames,
   the first and second images are alternately generated,
   a motion between the first and second images is detected, and
   one of the first and second images is continuously output or the first and second images are alternately output.

2. The optical scanning type observation apparatus according to claim 1, wherein the controller is further configured to:
   calculate an amount of motion of an image between different frames; and
   output both of the first and second images when the calculated amount of motion exceeds a predetermined threshold, or output one of the first and second images when the calculated amount of motion is equal to or below the predetermined threshold.

3. The optical scanning type observation apparatus according to claim 1, wherein
   the first scan route is a route from a center portion toward an outermost portion of a spiral-shaped scan route, and
   the second scan route is a route from the outermost portion toward the center portion of the spiral-shaped scan route.

4. A method for operating an optical scanning type observation apparatus, the method comprising:
   supplying illuminating light;
   guiding the illuminating light incident from an incident end portion of an optical fiber and emitting the illuminating light from an emission end portion of the optical fiber to an object;
   causing an irradiation position of the illuminating light emitted to the object to be displaced by swinging the emission end portion;
   controlling the emission end portion such that at least a first frame and a second frame are periodically obtained, a first scan route being drawn at the irradiation position in the first frame, a second scan route different from the first scan route being drawn at the irradiation position in the second frame;
   sequentially generating at least a first image in the first frame and a second image in the second frame, based on a signal obtained by receiving return light from the object to which the illuminating light is radiated;
   detecting a motion of an image between generated different frames; and
   based on a detected motion, outputting one of the first and second images or outputting both of the first and second images;
   the emission end portion is controlled so as to alternately obtain the first and second frames,
   the first and second images are alternately generated, a motion is detected between the first and second images, and one of the first and second images is continuously output or the first and second images are alternately output.

5. The method for operating the optical scanning type observation apparatus according to claim 4, wherein an amount of motion of an image is calculated between different frames generated in the generation step; and both of the first and second images are output when the calculated amount of motion exceeds a predetermined threshold, or one of the first and second images is output when the calculated amount of motion is equal to or below the predetermined threshold.

6. The method for operating the optical scanning type observation apparatus according to claim 4, wherein the first scan route is a route from a center portion toward an outermost portion of a spiral-shaped scan route, and the second scan route is a route from the outermost portion toward the center portion of the spiral-shaped scan route.

\* \* \* \* \*